US006592524B2

(12) United States Patent
Urbano et al.

(10) Patent No.: US 6,592,524 B2
(45) Date of Patent: Jul. 15, 2003

(54) TRANSMIT BEAMFORMER DELAY ARCHITECTURE AND METHOD FOR DIAGNOSTIC MEDICAL ULTRASOUND

(75) Inventors: Joseph A. Urbano, Audubon, PA (US); Albert Gee, Los Altos, CA (US); Kevin S. Randall, Ambler, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 256 days.

(21) Appl. No.: 09/748,527

(22) Filed: Dec. 22, 2000

(65) Prior Publication Data

US 2002/0082502 A1 Jun. 27, 2002

(51) Int. Cl.[7] .................................................. A61B 8/00
(52) U.S. Cl. ........................................................ 600/447
(58) Field of Search ................................. 600/437, 441, 600/440, 443, 444, 447; 73/625, 266; 367/7

(56) References Cited

U.S. PATENT DOCUMENTS

| | | | | | |
|---|---|---|---|---|---|
| 5,653,236 | A | * | 8/1997 | Miller | 600/447 |
| 5,675,554 | A | | 10/1997 | Cole et al. | |
| 5,740,128 | A | * | 4/1998 | Hossack et al. | 367/138 |
| 5,935,070 | A | * | 8/1999 | Dolazza et al. | 600/443 |
| 6,123,671 | A | * | 9/2000 | Miller | 600/447 |
| 6,312,386 | B1 | * | 11/2001 | Bolorforosh et al. | 600/447 |

* cited by examiner

*Primary Examiner*—Marvin M. Lateef
*Assistant Examiner*—Maulin Patel

(57) ABSTRACT

A transmit beamformer method and system is provided for applying absolute delays between groups of channels and applying relative delays to channels within the groups of channels. For example, every fourth channel is responsive to an absolute delay from a controller. The delay for channels between every fourth channel are set as relative delays corresponding to a further delay in addition to the absolute delay.

37 Claims, 3 Drawing Sheets

TRANSMIT BEAMFORMER DELAY ARCHITECTURE AND METHOD FOR DIAGNOSTIC MEDICAL ULTRASOUND

BACKGROUND

This invention relates to a transmit beamformer for a medical diagnostic ultrasound system. In particular, an architecture and method for implementing delays as a function of channel within an ultrasonic transmit beamformer are provided.

Transmit beamformers generate electrical waveforms in a plurality of channels for associated transducer elements of a transducer array. By applying different delays to different channels, a beam of ultrasound energy is steered and focused.

Transmit beamformers generate the transmit waveforms and apply delays for each channel separately. For example, U.S. Pat. No. 5,675,554 discloses applying a delay for each channel, such as shown in FIG. 3 of the '554 patent. An absolute delay for each channel is implemented by delaying a start of waveform generation or delaying the generated waveform. Transmit beamformers may use random access memories or first-in first-out buffers for each channel to delay the transmit waveform. A start-of-transmit signal is provided to each channel. In response to the absolute delays, the transmit waveform of each channel is delayed the same or differently than adjacent channels or other channels. Digital counters may be used to delay the start-of-transmit signal.

BRIEF SUMMARY

The present invention is defined by the following claims and nothing in this section should be taken as a limitation on those claims. By way of introduction, the preferred embodiments described below include a method and system for applying absolute delays between groups of channels and applying relative delays to channels within the groups of channels. For example, every fourth channel is responsive to an absolute delay from a controller. The delay for channels between every fourth channel are set as relative delays corresponding to a further delay in addition to the absolute delay.

In a first aspect, a method for ultrasound transmit beamforming is provided. Absolute delays are applied to at least two of a plurality of groups of channels and relative delays are applied to channels within each of the groups of channels.

In a second aspect, an ultrasound transmit beamformer system for focusing transmit beams is provided. A first plurality of channels comprise respective transmit pulse memories. A second plurality of channels without transmit memories but with delays are provided.

In a third aspect, an ultrasound transmit beamformer for focusing ultrasonic beams is provided. A plurality of programmable sequence generators for a first respective plurality of channels is provided. The programmable sequence generators operate as function of absolute delays. A plurality of relative delays are provided for a respective second plurality of channels. The channels of the second plurality of channels are different than the channels of the first plurality of channels.

Further aspects and advantages of the invention are discussed below in conjunction with the preferred embodiments.

DETAILED DESCRIPTION OF THE PREFERRED EMBODIMENTS

An absolute delay is provided for a sub-set of the channels of a transmit beamformer. For example, a counter responsive to a start-of-transmit signal is provided for every third channel. For other channels, a relative delay responsive to the absolute delay is provided. Unlike the absolute delay, the relative delay may be implemented by providing relatively small amounts of further delay between adjacent elements in addition to propogating the absolute delay.

The total amount of delay for any given channel is determined as a function of the transmit aperture, focal point and steering angle of a transmitted ultrasonic beam. For a given element, a transmit pulse may be delayed as a function of delays for adjacent elements. Larger steering angles require more delay between adjacent channels. The element pitch or distance between elements of the transducer array within the transmit aperture may also change the amount of delay between channels.

Figure 1:
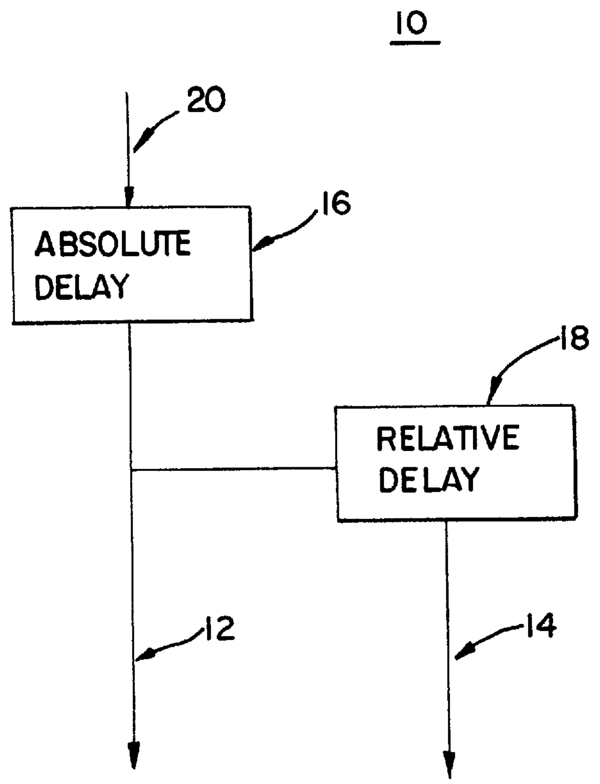
FIG. 1 is a block diagram of one embodiment of two transmit channels of a transmit beamformer.

FIG. 1 shows first and second channels 12, 14 of a transmit beamformer 10. The delay of the first channel 12 is provided by an absolute delay 16. The delay for the second channel 14 is provided by a relative delay 18 applied in addition to the absolute delay 16. The absolute delay 16 is responsive to a start-of-transmit signal 20. In response to the start-of-transmit signal 20, the absolute delay 16 delays generation or transmission of a waveform for channel 12. The relative delay 18 adds an additional delay to the absolute delay for generation or transmission of the waveform in the second channel 14. In one embodiment, the first and second channels 12, 14 comprise adjacent channels within a transmit beamformer for use with adjacent elements of a transducer array. The first and second channels 12, 14 may represent other channels, such as channels for non-adjacent transducer elements.

In one embodiment, the absolute and/or relative delays 16, 18 each comprise a counter, flip-flop, memory, random access memory, first-in first-out buffer or other analog or digital delay device. In one embodiment, the absolute delay 16 comprises a counter, and the relative delay 18 comprises a flip-flop logic device. Other combinations including the same or different components may be used.

In one embodiment, the delay signals on channels 12 and 14 are provided to respective transmit waveform generators for generating transmit waveforms. In alternative embodiments, the absolute and relative delays 16, 18 delay generated transmit waveforms. For example, a transmit waveform is provided to the absolute delay 16. The delayed transmit waveform outputted from the absolute delay 16 is provided on the first channel 12 and to the relative delay 18.

The relative delay 18 further delays the transmit waveform and outputs the transmit waveform on the second channel 14. As another example, transmit waveforms for each of the first and second channels 12, 14 are separately generated and delayed as a function of one or both of the absolute delay and relative delays 16, 18.

In one embodiment, the absolute delay 16 and/or relative delay 18 each include a transmit waveform generator, such as a programmable sequence generator. Analog circuitry, digital circuitry or combinations thereof are used to generate and transmit waveforms in response to an absolute delay. For example, a random access memory or other memory storing a sequence of samples representing the transmit waveform connects with a digital to analogue converter for generating the transmit waveform. As another example, the transmit waveform generator disclosed in U.S. Pat. No. 5,675,554, the disclosure of which is incorporated herein by reference, is used. In this embodiment, a memory stores an envelope of the transmit waveform. Various multipliers, summers, filters, interpolators and delays are used to generate a digital representation of a carrier wave modulated by the envelope samples. In alternative embodiments, the samples stored in the memory represent other characteristics of the waveform or the entire transmit waveform.

The transmit waveform generator is programmable in one embodiment. For example, the analog or digital circuitry for generating the transmit waveform may be changed or responsive to information from a controller to generate different transmit waveforms, such as different frequencies, amplitudes, envelopes, durations, or the characteristics. Alternatively, one or more set waveforms may be generated by the transmit waveform generator.

In one embodiment, one, more, or all of the channels are implemented on a single or multiple logic devices. For example, a programmable logic device, such as a field programmable gate array (FPGA), is used to generate the transmit waveforms as well as apply absolute and relative delays. Using the memory or random access memory blocks within a FPGA, such as an Altera, 10K or 20K FPGA, samples for a transmit waveform are stored. Flip-flops provided in the FPGA apply the absolute and relative delays. In one embodiment, some, most, or all of the available ram blocks within the FPGA are assigned to a sub-set of the channels, the sub-set corresponding to channels responsive to just an absolute delay. Flip-flops are assigned to each of the channels to implement the absolute and relative delays of other channels. Multiplexers may be used to select the delay time. Additional flip-flops may be used to provide pipelining of the multiplexer to alleviate timing problems caused by propagation delays through the logic elements of the field programmable gate array.

Alternatively, an application specific integrated circuit, individual hardware components, a digital signal processor, a processor responsive to software or analog components are used to implement any one or more of the various counters, memories, delays and multiplexers discussed herein.

Figure 2:
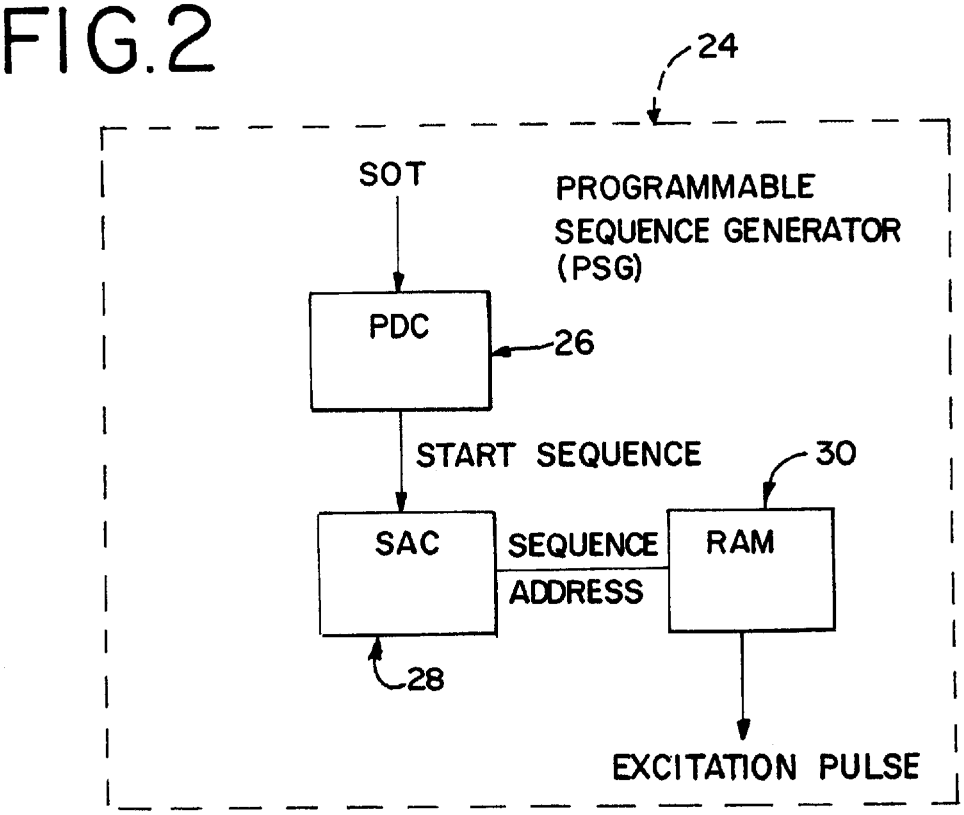
FIG. 2 is a block diagram of one embodiment of a programmable sequence generator used for applying absolute delays.

In one embodiment, the absolute delay 16 is implemented as a programmable sequence generator shown in FIG. 2. The relative delay 18 is implemented as a relative delay shown in FIG. 3. Referring to FIG. 2, the programmable sequence generator 24 comprises a programmable delay counter 26, a sequence address counter 28 and a RAM 30. In one embodiment, the programmable sequence generator 24 is implemented on a programmable logic device. In alternative embodiments, other devices or individual components may be used. Different components for generating waveform samples responsive to an absolute delay may be used, such as analog or other digital devices.

The absolute delay is programmed into the programmable delay counter 26. In response to a start-of-transmit signal, the programmable delay counter 26 counts a number of clock cycles associated with the absolute delay. After the absolute delay time period, a start sequence signal is provided to the sequence address counter 28.

The sequence address counter 28 counts through RAM addresses until the transmit waveform sequence is output as an excitation pulse. The sequence address counter 28 may periodically loop through the address sequence for each transmit waveform. The sequence address 20 may be programmed with various data widths or RAM address ranges for generating the transmit waveform. Larger data widths or address ranges provide added flexibility in shaping the transmit waveform. As discussed above, the samples output from the RAM 30 are converted to analog signals or further processed to generate the transmit waveform.

Figure 3:
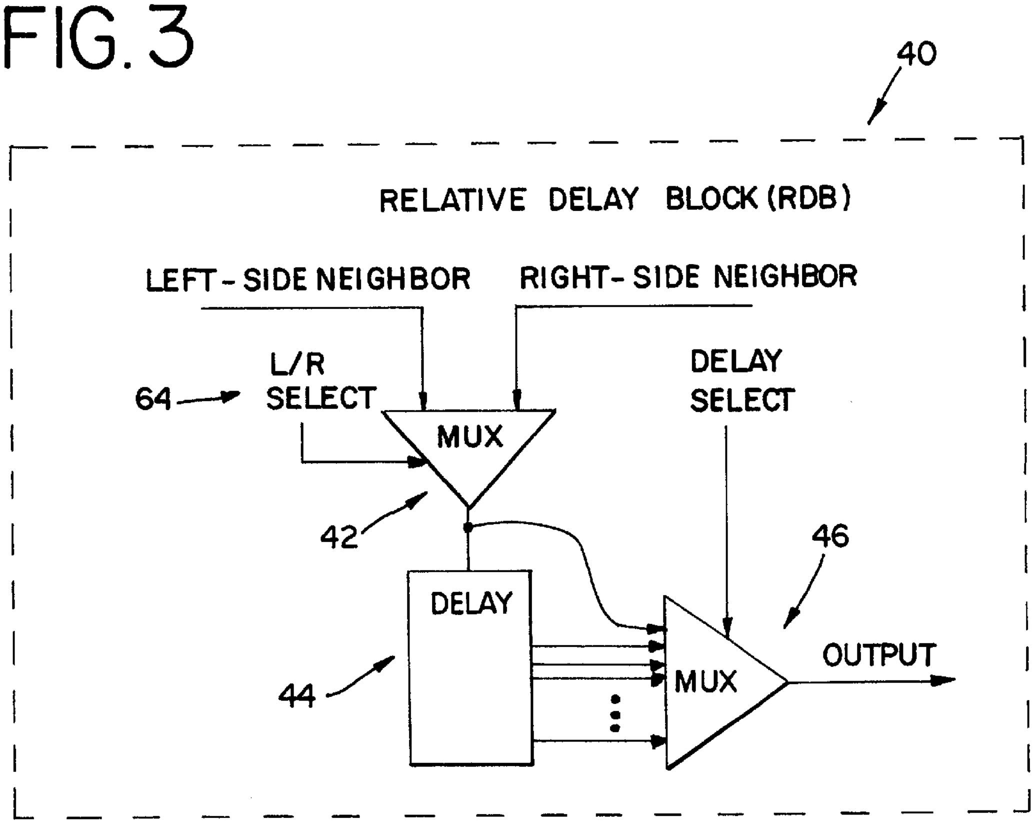
FIG. 3 is a block diagram of one embodiment of a relative delay for applying a relative delay.

FIG. 3 shows a relative delay 40 implemented on a field programmable gate array, other logic device, processor, individual components or software. The relative delay 40 includes a channel-selection multiplexer 42, relative delay 44, a delay multiplexer 46, propagation delay 48 and a propagation multiplexer 50. Additional or fewer multiplexers or delays may be provided. In alternative embodiments, the relative delay 40 includes a transmit pulse generator.

The channel select multiplexer 42 comprises a two-to-one input multiplexer for selecting between delay signals, transmit waveforms or transmit waveform samples output from adjacent channels. In alternative embodiments, non-adjacent channels or more than two channels may be input. In yet another alternative embodiment, only a single channel is input and the channel select multiplexer is not used. By selecting between the transmit waveform outputs of adjacent or other channels, the relative delay block may operate without a pulse memory or transmit waveform generator. In alternative embodiments, the relative delay 40 receives delay information from an adjacent channel, applies a further relative delay, and generates a transmit waveform.

The selected transmit waveform information is delayed by the relative delay 44. The relative delay 44 comprises a plurality of flip-flops or other delay devices. Each of the flip-flops and a signal output directly from the channel select multiplexer 42 provide respective outputs associated with different amounts of delay to the delay selection multiplexer 46.

The delay selection multiplexer 46 is programmed to select a particular output associated with a desired relative delay. The relative delay is selected as a function of the steering angle, element pitch of the transducer array and the delay applied to the selected input into the relative delay 40. The relative delay 44 includes a sufficient number of flip-flops to implement a relative or further delay from the selected channel for a maximum possible steering angle and a given element pitch.

There may be an inherent signal propagation delay through the delay selection multiplexer 46 even for the "zero delay" path. This is referred to as pipeline delay. For a digitally sampled transmit waveform, the delay selection multiplexer 46 may contain internal flip-flops to implement pipeline delays and/or an additional flip-flop or other delay at the output of the delay selection multiplexer 46. These flip-flops are added to allow the digital logic to operate at a clock period that is shorter than the maximum signal propagation delay time through the multiplexer circuitry.

Figure 4:
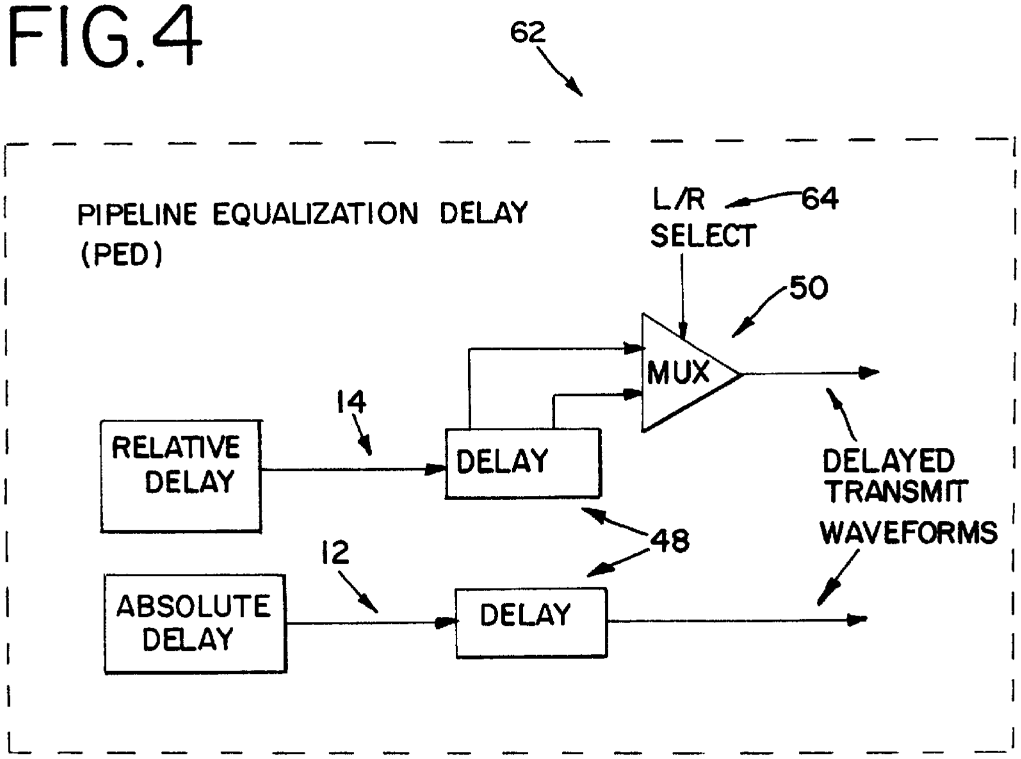
FIG. 4 is a block diagram of one embodiment of a pipelined equalization delay.

In one embodiment shown in FIG. 4, a pipeline equalization delay stage 62 is added at the output of every channel to account for these pipeline delays. This provides for an effective zero relative delay path between channels. The amount of pipeline equalization delay depends on the direction the transmit waveform is propagating from (i.e. left or right) as well as the elements location within the group of channels responsive to the same absolute delay (relative delay group). The output of each absolute delay channel 12 is input to the pipeline equalization delay 62. The amount of delay is fixed at the overall pipeline delay of a transmit waveform that propagates from one end of the relative delay group to the other end while all relatives delays are programmed as zero. This ensures that the actual relative delay between the absolute delay channel 12 and the channel furthest from the absolute delay channel 12 in the group is zero. The pipeline equalization delay may be implemented as a series of flip-flops or other delay components, such as provided by the propagation delay 48.

Following each relative delay channel 14 within the relative delay group, two pipeline equalization delays are generated by a propagation delay 48, one for left-side propagation and one for right-side propagation. These two propagation delays are generally different from one another but are the same for a channel in the exact center of the group where the group comprises an odd number of channels. The two delayed transmit waveforms are provided to the input ports of a two-to-one multiplexer 50. The multiplexer output is selected by the left/right select signal 64. By minimizing the number of channels within a relative delay group, the number of flip-flops or additional pipeline equalization delays 48 is minimized. The output of the pipeline equalization delay 62 is provided to the transducer element or further processed to generate or alter a transmit waveform that is applied to the transducer element.

Figure 5:
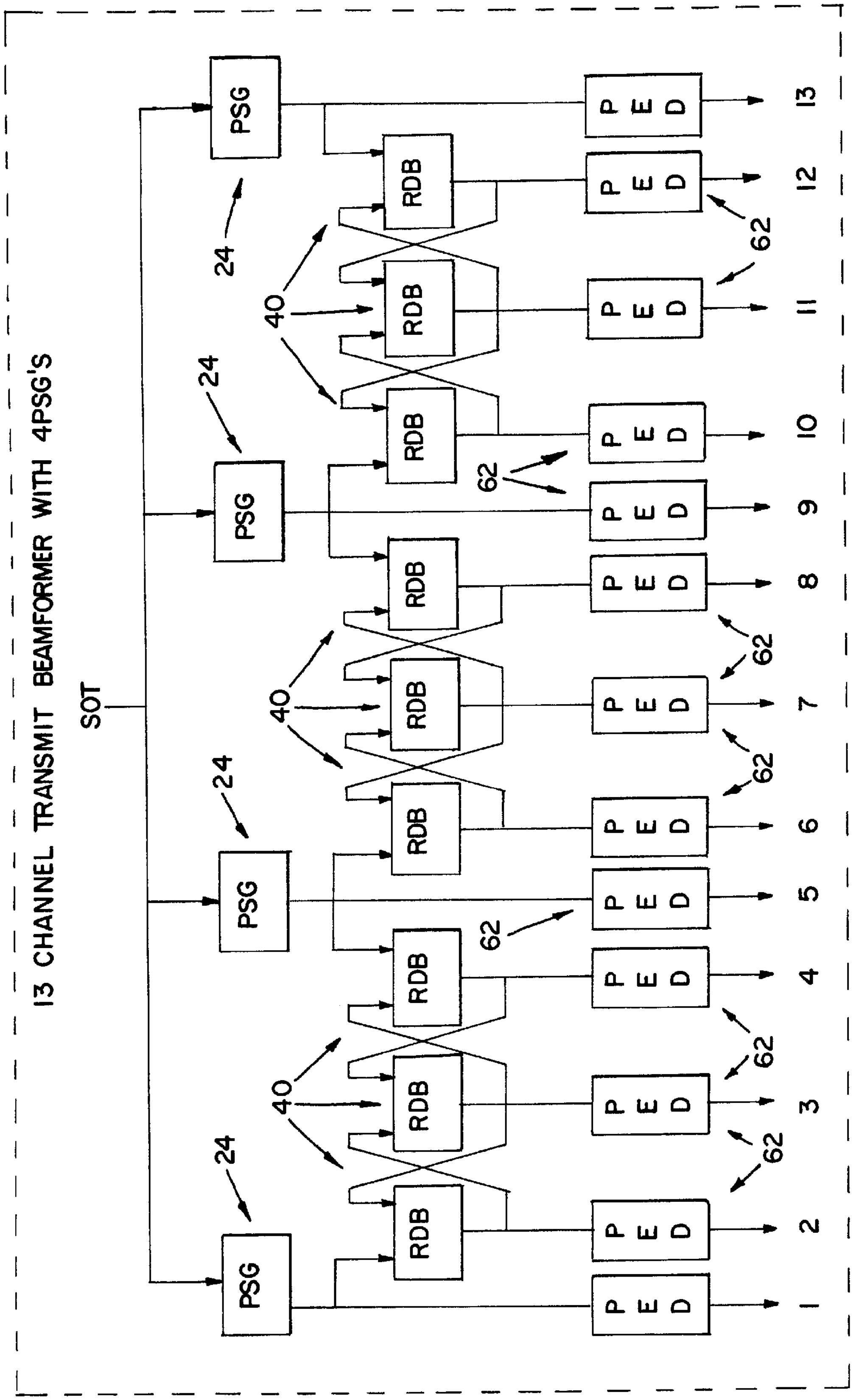
FIG. 5 is a block diagram of one embodiment of a plurality of channels in a transmit beamformer.

FIG. 5 shows a transmit beamformer 60 comprising 13 channels. More or fewer channels may be provided. For purposes of this discussion, each channel is assumed to be within the transmit aperture. Each channel is associated with one of a programmable sequence generator 24 or a relative delay 40. Each channel is associated with one of an absolute delay 16 or a relative delay 18. As discussed above, the programmable sequence generator 24 applies an absolute delay, and the relative delay 40 applies a relative delay.

The programmable sequence generators 24 are distributed throughout the transmit beamformer. For example, every N-channel comprises a programmable sequence generator 24. As shown in FIG. 4, every fourth channel comprises a programmable sequence generator 24. N maybe more or less or vary as a function of position along the transmit aperture. In one embodiment, the channels at the end of the aperture include programmable sequence generators 24 at the ends of the transmit beamformer, such as channels 1 and 13 of the transmit beamformer 60. The remaining programmable sequence generators are distributed evenly throughout the transmit beamformer, such as at channels 5 and 9. The even distribution of the programmable sequence generators 24 through the channels of the transmit beamformer 60 minimizes the number of relative delays 40 between each pair of programmable sequence generators 24. As shown in FIG. 4, three relative delays 40 are provided for each of the three respective channels between each programmable sequence generator 24. Other distributions of the programmable sequence generators 24 for applying an absolute delay may be used.

In response to a start-of-transmit signal, each of the programmable sequence generators 24 applies an absolute delay and generates a transmit waveform or signal representing a characteristic of the transmit waveform. The absolute delay applied for each of the channels is different or the same. Optional pipeline equalization delays 62 may be provided for the channels associated with a programmable sequence generator 24. The pipeline equalization delay 62 compensates for added pipeline or propagation delay through the relative delays 40 associated with each absolute delay. In alternative embodiments, pipeline equalization delays 62 are provided for all of the channels 12, 14 as shown in FIG. 5. The pipeline equalization delay 62 may be provided to other subsets of channels within the transmit aperture.

Each relative delay 40 and associated channel is grouped with one of the programmable sequence generators 24 and its associated channel. Each relative delay 40 is operable to select the output from one of two adjacent channels. For example, the relative delay 40 of channel 2 may select as an input the output of the programmable sequence generator 24 of channel 1. The relative delay 40 of channel 3 may select the output of the relative delay 40 of channel 2. The relative delay 40 of channel 4 and channel 6 may select the output of the programmable sequence generator 24 of channel 5. For this subset of channels, two groupings of channels are provided where each grouping is responsive to a different programmable sequence generator 24 and an associated absolute delay. To minimize the possible relative delay between channels implemented by the relative delays 40, the relative delays 40 receive as input the output from adjacent channels. Other groupings, whether programmed or set, may be used.

To focus and steer ultrasonic energy, the transmit beamformer 60 programs the programmable sequence generator 24 with absolute delays. The relative delays 40 are programmed to select an input, defining the groupings of channels responsive to each of the absolute delays. The relative delays 40 are also programmed with a further relative delay as a function of the corresponding absolute delay and any further relative delays added to the selected input. The delay information, transmit waveforms, signal representing a characteristic of the transmit waveform, or other information output on each channel is delayed in the channels to provide appropriate steering and focusing.

To provide the appropriate delays for each channel, a common synchronous clock is provided to both the programmable sequence generators 24 and the relative delays 40. In alternative embodiments, the relative delays 40 are operated at a clock frequency that is an integer multiple of the clock frequency provided to the programmable sequence generator 24. For implementation on a field programmable gate array, 64 or more channels may be provided at a high clock rate where a limited amount of RAM for generating transmit waveform samples is used in a sub-set of all of the channels. For example, various relative delays 40 are provided as discussed above.

While the invention has been described above by reference to various embodiments it will be understood that many changes and modifications can be made without departing from the scope of the invention. Any hardware and software may be used to implement one or more of the components and apply one or more relative and absolute delays. The groupings of channels may be set or programmable. Any number of channels may be provided for the transmit beamformer.

It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A method for ultrasound transmit beamformation, the method comprising:

(a) applying absolute delays to at least one of a plurality of groups of channels; and (b) applying relative delays to channels within each of the plurality of groups of channels, the relative delays for the at least one group being a function of at least one of the absolute delays.

2. The method of claim 1 wherein (a) comprises applying absolute delays to each the plurality of groups of channels.

3. The method of claim 1 wherein (b) comprises applying relative delays to each channel within each of the plurality of groups of channels.

4. The method of claim 1 further comprising:

(c) generating transmit pulses responsive to a programmable envelope.

5. The method of claim 1 further comprising:

(c) implementing the delays with logic in a programmable logic device; and (d) storing transmit pulse envelope or sequence in a memory of the programmable logic device.

6. The method of claim 1 wherein (a) comprises delaying with first and second counters for first and second channels of first and second groups of channels, respectively.

7. The method of claim 1 wherein (b) comprises delaying a transmit pulse from an output of an adjacent channel.

8. The method of claim 1 wherein (b) comprises:

(b1) selecting an output from one of two adjacent channels;

(b2) delaying the output with a logic device.

9. The method of claim 1 further comprising:

(c) minimally delaying each channel associated with a multiplexer at least one clock cycle.

10. The method of claim 1 wherein (a) comprises delaying generation of a transmit pulse differently for every N channel where N is greater than two and less than or equal to half the channels used for a transmit aperture and (b) comprises delaying the transmit pulse output by the N channel within the group of channels for a second channel within the group of channels.

11. The method of claim 10 wherein every N channel comprises every fourth channel.

12. The method of claim 1 further comprising:

(c) selecting an output from one of at least two channels for application of the relative delay.

13. A ultrasound transmit beamformer system for focusing transmit beams, the system comprising:

a first plurality channels with respective transmit pulse memories; and a second plurality of channels without transmit pulse memories and with delays.

14. The system of claim 13 further comprising:

a counter for each of the first plurality of channels, the counters responsive to a start-of-transmit signal and the transmit pulse memories responsive to the counters.

15. The system of claim 14 wherein each counter comprises a programmable delay counter and a memory sequence address counter.

16. The system of claim 13 wherein each of the first plurality of channels further comprises a delay operatively connected with an output of the transmit pulse memories.

17. The system of claim 13 wherein each of the second plurality of channels further comprises a multiplexer operatively connected with the outputs of at least two other channels and the delays.

18. The system of claim 17 wherein the multiplexer of at least one channel operatively connects with an output from one of the first plurality of channels.

19. The system of claim 13 wherein each delay comprises a plurality of delay elements and a multiplexer operatively connects with an output of the plurality of delay elements in the channel.

20. The system of claim 19 further comprising a delay connected with an output of the multiplexer.

21. The system of claim 13 wherein the transmit pulse memory is operative to store a transmit pulse sequence.

22. The system of claim 13 wherein the first plurality of channels comprise every N channel of a transmit aperture and the second plurality of channels comprises groups of channels between pairs of the first plurality of channels, each group of channels of the second plurality of channels operatively connected with an associated pair of the first plurality of channels.

23. The system of claim 22 wherein N is four and each group of the second plurality of channels comprise three channels.

24. The system of claim 13 wherein the transmit pulse memories and the delays comprises logic in a programmable logic device.

25. The system of claim 24 wherein the programmable logic device comprises a field programmable gate array.

26. The system of claim 24 wherein the first and second plurality of channels defined as a function of programming the programmable logic device.

27. An ultrasound transmit beamformer for focusing ultrasonic beams, the transmit beamformer comprising:

a plurality of programmable sequence generators for a respective first plurality of channels, the programmable sequence generators operable as a function of absolute delays; and a plurality of relative delays for a respective second plurality of channels, the channels of the second plurality of channels different than the channels of the first plurality of channels.

28. The transmit beamformer of claim 27 wherein each programmable sequence generator comprises a counter and a memory responsive to the counter, the counter operable to provide one of the absolute delays.

29. The transmit beamformer of claim 28 wherein the relative delays operatively connect with respective outputs of respective memories, the relative delays operable to delay the outputs relative to the absolute delays.

30. The transmit beamformer of claim 27 wherein each of the second plurality of channels further comprises a first multiplexer operatively connected with the relative delay.

31. The transmit beamformer of claim 30 wherein each of the second plurality of channels further comprises a second multiplexer operable to select one of a plurality of relative delay outputs.

32. The transmit beamformer of claim 27 wherein the programmable sequence generators and the relative delays comprise components of a programmable logic device.

33. The transmit beamformer of claim 32 wherein the programmable logic device comprises a field programmable gate array.

34. The transmit beamformer of claim 27 wherein the relative delays operatively connect to receive an output of the programmable sequence generator.

35. The transmit beamformer of claim 34 wherein a first relative delay operatively connects with the output of the programmable sequence generator and a second relative delay operatively connects with an output of the first relative delay.

36. The transmit beamformer of claim 27 wherein the first plurality of channels comprise every N channel, where N is at least two and less than or equal to half the total number of channels, and wherein the second plurality of channels comprises groups of channels between pairs of the first plurality of channels.

37. The transmit beamformer of claim 36 wherein N comprises four.

* * * * *